(12) United States Patent
Costa et al.

(10) Patent No.: US 8,377,888 B2
(45) Date of Patent: Feb. 19, 2013

(54) METHOD OF PREDICTING THE CLINICAL RESPONSE TO CISPLATIN OR CARBOPLATIN CHEMOTHERAPEUTIC TREATMENT

(75) Inventors: Rafael Rosell Costa, Badalona (ES); Miguel Taron Roca, Badalona (ES)

(73) Assignee: Pangaea Biotech, S.A., Barcelona (ES)

( * ) Notice: Subject to any disclaimer, the term of this patent is extended or adjusted under 35 U.S.C. 154(b) by 219 days.

(21) Appl. No.: 11/908,796

(22) PCT Filed: Mar. 16, 2006

(86) PCT No.: PCT/EP2006/002610
§ 371 (c)(1),
(2), (4) Date: Nov. 14, 2007

(87) PCT Pub. No.: WO2006/097346
PCT Pub. Date: Sep. 21, 2006

(65) Prior Publication Data
US 2009/0068657 A1 Mar. 12, 2009

(30) Foreign Application Priority Data
Mar. 16, 2005 (EP) .................................... 05075632

(51) Int. Cl.
*A61P 35/00* (2006.01)
*C12Q 1/68* (2006.01)
(52) U.S. Cl. ........................ 514/19.3; 435/6.11; 435/6.12
(58) Field of Classification Search .......................... None
See application file for complete search history.

(56) References Cited

FOREIGN PATENT DOCUMENTS

| KR | 20030069752 A | | 8/2003 |
|---|---|---|---|
| WO | 02059347 A2 | | 8/2002 |
| WO | WO03/052135 | * | 6/2003 |
| WO | 2005012569 A1 | | 2/2005 |
| WO | WO2005/0474511 | * | 5/2005 |

OTHER PUBLICATIONS

NLM Gateway Mesh Term Information (downloaded from the Web on Jun. 8, 2009).*
"Accession No. GSN: ADQ77506—PCR primer amplifies promoter CpG islands of cancer related genes seq188", "Database Geneseq [Online]", Sep. 9, 2004.
Boulikas, Teni, et al., "Recent clinical trials using cisplatin, carboplatin and their combination chemotherapy drugs (Review)", "Oncology Reports", Mar. 2004, pp. 559-595, vol. 11, No. 3.
Clegg, A., et al., "Clinical and cost effectiveness of paclitaxel, docetaxel, gemcitabine, and vinorelbine in non-small cell lung cancer . . .", "Thorax", Jan. 2002, pp. 20-28, vol. 57, No. 1.
Esteller, Manel, et al., "Detection of aberrant promoter hypermethylation of tumor suppressor genes in serum DNA from non-small cell lung cancer.", "Cancer Research", Jan. 1, 1999, pp. 67-70, vol. 59.
Ferguson, Anne T., et al., "High frequency of hypermethylation at the 14-3-3 sigma locus leads to gene silencing in breast cancer", "Proceedings of the National Academy of Sciences (USA)", May 23, 2000, pp. 6049-6054, vol. 97, No. 11.
Herman, James G., et al., "Methylation-specific PCR: a novel PCR assay for methylation status of CpG islands", "Proc. Natl. Acad. Sci.", Sep. 1, 1996, pp. 9821-9826, vol. 93, Published in: Washington, D.C., US.
Osada, Hirotaka, et al., "Frequent and histological type-specific inactivation of 14-3-3sigma in human lung cancers", "Oncogene", Apr. 4, 2002, pp. 2418-2424, vol. 21, No. 15.
Ramirez, JL, et al., "Serum DNA as a tool for cancer patient management", "Roczniki Akademii Medycznej w Bialymstoku", 2003, pp. 34-41, vol. 48.
Ramirez, Jose Luis, et al., "14-3-3sigma methylation in pretreatment serum circulating DNA of cisplatin-plus-gemcitabine-treated advanced non-small..", "Journal of Clinical Oncology", Dec. 20, 2005, pp. 9105-9112, vol. 23, No. 36, Publisher: American Society of Clinical Oncology.
Rosell, Rafael, et al., "Nucleotide excision repair pathways involved in cisplatin resistance in non-small-cell lung cancer", "Cancer Control: Journal of the Moffitt Cancer Center", Jul. 2003, pp. 297-305, vol. 10, No. 4.
Sathyanarayana, Ubaradka G., et al., "Establishment and validation of quantitative real-time PCR assay for aberrant methylation of 14-3-3 sigma gene in . . .", "Cancer Genomics and Proteomics", Feb. 2004, pp. 1-8, vol. 1, No. 1.
Sorenson, Sverre, et al., "A systematic overview of chemotherapy effects in non-small cell lung cancer", "Acta Oncologia", 2001, pp. 327-339, vol. 40, No. 2-3, Published in: Stockholm.
Teodoridis, Jens M., et al., "Epigenetic silencing mediated by CpG island methylation: potential as a therapeutic target and as a biomarker", "Drug Resistance Updates", 2004, pp. 267-278, vol. 7, No. 4-5.
Wei, Susan H., et al., "Aberrant DNA methylation in ovarian cancer", "Ann. N.Y. Acad. Sci.", Mar. 2003, pp. 243-250, vol. 983, Published in: New York, New York.

* cited by examiner

*Primary Examiner* — Karen Canella
(74) *Attorney, Agent, or Firm* — Hultquist, PLLC; Kelly K. Reynolds; Steven J. Hultquist

(57) ABSTRACT

Method for predicting the survival of a patient suffering from NSCLC to a cisplatin or carboplatin based chemotherapy treatment which comprises the step of determining the methylation state of a nucleic acid encoding 14-3-3 sigma in a biological sample from the patient, wherein the presence of methylation is indicative of longer survival of said patient as a response to said chemotherapy treatment. The methylation status of the 14-3-3 sigma gene can be easily determined in a serum sample.

7 Claims, 3 Drawing Sheets

US 8,377,888 B2

METHOD OF PREDICTING THE CLINICAL RESPONSE TO CISPLATIN OR CARBOPLATIN CHEMOTHERAPEUTIC TREATMENT

CROSS REFERENCE TO RELATED APPLICATIONS

This application is filed under the provisions under the provisions of 35 USC 371 based on International Application PCT/ES2006/002610 filed Mar. 16, 2006, which in turn claims priority of European Patent Application 05075632.9 filed Mar. 16, 2005. The disclosures of such International Application and European priority application are hereby incorporated herein by reference in their respective entireties, for all purposes.

FIELD OF THE INVENTION

The present with him invention relates to the field of diagnostics, in particular to a method for predicting the survival of non small cell lung carcinoma (NSCLC) patients, based on the methylation pattern of the gene 14-3-3 sigma. It also relates to the use of chemotherapeutic agents for the treatment of NSCLC patients.

BACKGROUND OF THE INVENTION

Non-small-cell lung cancer (NSCLC) accounts for approximately 80% of all lung cancers, with 1.2 million new cases worldwide each year. NSCLC resulted in more than one million deaths worldwide in 2001 and is the leading cause of cancer-related mortality in both men and women (31% and 25%, respectively). The prognosis of advanced NSCLC is dismal. A recent Eastern Cooperative Oncology Group trial of 1.155 patients showed no differences among the chemotherapies used: cisplatin/paclitaxel, cisplatin/gemcitabine, cisplatin/docetaxel and carboplatin/paclitaxel. Overall median time to progression was 3.6 months, and median survival was 7.9 months, a 1-year survival rate of 33% and a 2-year survival rate of 11 percent. A more recent randomized study of 1218 patients reported a median survival of 11 months in stage IIIB-IV patients. However, no clinical parameters can completely account for the striking differences in survival among patients with advanced disease, with some surviving years and others only a few months.

The overall five-year survival of patients with NSCLC has remained at less than 15% for the past 20 years. Stage grouping of TNM subsets (T=primary tumor; N=regional lymph nodes; M=distant metastases) permits the identification of patient groups with similar prognosis and treatment options. Five-year survival is around 25% for pathologic stage IIB (T1-2N1M0, T3N0M0), 13% for stage IIIA (T3N1M0, T1-2-3N2M0), and a low 7% for stage IIIB (T4N0-1-2M0).

Currently, cisplatin (DDP) and carboplatin are among the most widely used cytotoxic anticancer drugs. However, resistance to these drugs through de novo or induced mechanisms undermines their curative potential. These drugs disrupt DNA structure through formation of intrastrand adducts. Resistance to platinum agents such as DDP has been attributed to enhanced tolerance to platinum adducts, decreased drug accumulation, or enhanced DNA repair.

14-3-3σ is a member of the 14-3-3 superfamily that is responsible for $G_2$ cell cycle checkpoint control in response to DNA damage in human cells. Its function has been analyzed in the human colorectal cancer cell line HCT116 (expressing 14-3-3σ and wild-type p53). Following ionizing irradiation, 14-3-3σ sequestered Cdc2/cyclin B1 complexes in the cytoplasm, thus arresting cells in $G_2$ and preventing them from initiating mitosis before repair to their damaged DNA. Colon carcinoma cells lacking 14-3-3σ treated with adriamycin can still initiate—but do not maintain—G2 arrest, leading to mitotic catastrophe and cell death. The expression of 14-3-3σ is reduced by p53 gene inactivation and by silencing of 14-3-3σ gene via methylation of CpG islands.

By proteomic analysis, 14-3-3σ was undetectable in breast cancer samples, and hypermethylation of normally unmethylated CpG islands in the promoter region of 14-3-3σ was involved in gene silencing at the transcriptional level in breast cancers (Ferguson A T, Evron E, Umbricht C B, et al.: High frequency of hypermethylation at the 14-3-3 sigma locus leads to gene silencing in breast cancer. *Proc Natl Acad Sci USA* 2000; 97:6049-54). Similar effects of 14-3-3σ hypermethylation have been reported in many tumors, including lung, gastric, ovarian, prostate, and hepatocellular carcinomas.

It is known that double-stranded DNA fragments frequently occur in considerable quantities in the serum of cancer patients, with significantly higher levels found in the serum of patients with metastases. In head and neck, small-cell lung and non-small-cell lung cancers, the same microsatellite alterations detected in the tumor were also found in plasma or serum DNA (Sanchez-Cespedes M, Monzo M, Rosell R, et al. Detection of chromosome 3p alterations in serum DNA of non-small-cell lung cancer patients. *Ann Oncol* 1998; 9:113-6; Sozzi G, Musso K, Ratcliffe C, Goldstraw P, Pierotti M A, Pastorino U. Detection of microsatellite alterations in plasma DNA of non-small cell lung cancer patients: a prospect for early diagnosis. *Clin Cancer Res* 1999; 5:2689-92). Furthermore, the detection of hypermethylation in the promoter regions of tumor suppressor genes was first reported in the serum of non-small-cell lung cancer patients. Hypermethylation can be analyzed by the sensitive methylation-specific polymerase chain reaction assay, which can identify one methylated allele in 1000 unmethylated alleles (Herman J G, Graff J R, Myohanen S, Nelkin B D, Baylin S B. Methylation-specific PCR: a novel PCR assay for methylation status of CpG islands. *Proc Natl Acad Sci* USA 1996; 93:9821-6).

14-3-3σ was found to be methylated in 43 percent of 60 gastric cancers and the 14-3-3σ methylation-positive human gastric cell lines MKN74 (with wild-type p53) and MKN28 (with mutated p53) were both highly sensitive to adriamycin, while 14-3-3σ methylation-negative cell lines (either with wild-type or mutated p53) were resistant.

While no major overall impact can be attained with traditional chemotherapy in NSCLC, as explained before, it is clear that chemosensitivity and thus survival is individually predetermined. Nevertheless, in spite of the growing list of genetic abnormalities identified as being involved in DNA repair pathways and altered chemosensitivity in NSCLC patients, translational assays have not yet been developed for use in individualized chemotherapy.

It is an object of the present invention to provide predictors of response to chemotherapy, which can be a valuable clinical tool for use in the selection of optimal treatment modes, in particular for patients like those suffering from NSCLC, having such a poor survival rate and unpredictable chemosensitivity.

SUMMARY OF THE INVENTION

The present invention provides a tool for use in predicting differential survival and chemosensitivity, and tailoring chemotherapy in NSCLC.

Drug resistance is a complex and multifactorial event involving activation/repression of multiple biochemical pathways. We used a proteomic approach to study cisplatin resistance and drug response. Starting from the assumption that defects in the cell cycle checkpoint may contribute to chemosensitivity, we investigated whether patients with 14-3-3σ methylation-positive tumors could derive greater benefit from cisplatin- or carboplatin-based chemotherapy.

Surprisingly, we found that 14-3-3σ is methylated in the sera of one-third of non-small-cell lung cancer patients and that methylation is related to significantly better median survival for these patients overall. Furthermore, 14-3-3σ methylation had an even greater influence on survival in responders. The risk of death for 14-3-3σ methylation-negative responders was almost five times that of methylation-positive responders.

In one aspect, the present invention is directed to an in vitro method for predicting the survival following cisplating or carboplatin based chemotherapy of a patient suffering from non-small-cell lung cancer (NSCLC) comprising the steps:
  a) isolating nucleic acids from a body fluid, serum or tissue sample of the patient;
  b) establishing the methylation state of the nucleic acid encoding 14-3-3 sigma in the sample,
  c) and classifying the patients in 2 groups defined as methylation-positive or methylation-negative according to the results,
wherein to each group a prognosis relating to survival is established.

In another aspect, the invention is directed to a method for predicting the survival of a patient suffering from NSCLC to a cisplatin or carboplatin based chemotherapy treatment which comprises the step of determining the methylation state of a nucleic acid encoding 14-3-3 sigma in a biological sample from the patient, wherein the presence of methylation is indicative of longer survival of said patient as a response to said chemotherapy treatment.

In a further aspect, the invention relates to a method for designing an individual chemotherapy treatment based on cisplatin or carboplatin for a subject suffering from NSCLC which comprises:
  i) determine the methylation state of a nucleic acid encoding 14-3-3 sigma in a biological sample from the patient;
  ii) considering the data obtained in the previous step for designing an individual chemotherapy treatment.

The invention also relates to a kit and its use for predicting the survival to chemotherapeutic treatment of a NSCLC patient, wherein the kit comprises a first container containing a reagent which modifies unmethylated cytosine and a second container containing primers for amplification of a CpG-containing nucleic acid of the 14-3-3 gene, wherein the primers distinguish between modified methylated and nonmethylated nucleic acid.

It is important to note that in one embodiment of the invention the methylation of 14-3-3σ can be detected in pre-treatment body fluids of non-small-cell lung cancer patients, obviating the need for tumor tissue and offering a novel and accurate method to select patients for cisplatin-based chemotherapy and to predict survival after treatment with platinum-based doublets. Preferably the body fluid is serum.

Thus in another aspect the invention is directed to the determination of the methylation status of the 14-3-3 sigma gene in a sample from a mammal, characterised in that the sample is a serum sample.

DETAILED DESCRIPTION OF THE INVENTION

Figure 1:
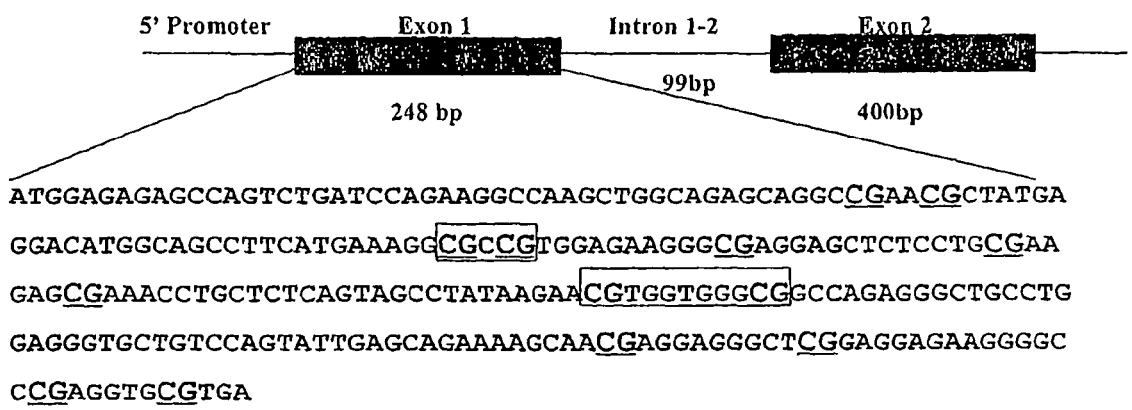
FIG. 1. 14-3-3σ gene structure and DNA sequence from exon 1. CpG sites containing are highlighted and CpG dinucleotides tested for methylation by methylation-specific polymerase chain reaction are indicated by boxes (CpG dinucleotides 3 and 4 in the forward primer and CpG dinucleotides 8 and 9 in the reverse primer).

Cisplatin is still the scaffolding of combination chemotherapy in non-small cell lung cancer (NSCLC). Results tend to be similar whether the partner drug is paclitaxel, docetaxel, or gemcitabine. Similar results are generally obtained with carboplatin, although in a randomized study, median survival was 8.2 months in the paclitaxel/carboplatin arm and 9.8 months in the paclitaxel/cisplatin arm.

Many citotoxic drugs induce DNA damage similar to that caused by carcinogens. Covalent binding of the carcinogen or cytotoxic drug results in the formation of a chemically altered base in DNA that is termed an "adduct". Cisplatin has a rigid structure with two labile chloro and two stable amine ligands in a cis configuration. Like some alkylating agents, the neutral drug molecule needs to be converted to a reactive form. This occurs nonenzymatically in solution, where displacement reactions result in stepwise exchange of the labile chloro ligands with water molecules. The charged aquated species are highly reactive, but the chloro-monoaquo species is the most significant from the perspective of interaction with DNA at physiological pH. In the case of carboplatin, which is a more stable bidentate cyclobutanedicarboxylate ligand, the aquation reaction is much slower. This reduces drug potency, which thereby requires a greater dose for an equivalent antitumor effect. As soon as the monoaquated species of cisplatin is formed, it reacts immediately with a DNA base (preferentially N7 of guanine) to form a monofunctional adduct. The remaining chloride ligand linked to platinum in the monoadduct is then hydrolyzed, and the resulting aquated species interacts with a second nucleophilic site to form DNA cross-links. Both 1,2- and 1,3-intrastrand DNA cross-links are formed. 1,2-interstrand cross-links between opposite guanine bases are formed preferentially in 5'G-C3' sequences of both strands. However, mounting evidence indicates that intrastrand adducts provide the strongest basis for the cytotoxic action of cisplatin.

Cisplatin generally is formulated as a sterile solution for injection, and is routinely administered at a dose of about 50 to 100 mg/m$^2$, given intravenously. This cycle can be repeated for about every 4 to 8 weeks.

Although cisplatin and carboplatin are widely used for NSCLC patients, resistance to these drugs through de novo or induced mechanisms undermines their curative potential. In general, the genetic mechanisms of cancer chemoresistance are difficult to understand. During the past 30 years medical oncologists have focused to optimise the outcome of cancer patients and it is just now that the new technologies available are allowing to investigate polymorphisms, gene expression levels and gene mutations aimed to predict the impact of a given therapy in different groups of cancer patients to tailor chemotherapy.

To further improve the survival rate in patients with Non-Small Cell Lung Carcinoma (NSCLC), their prognostic classification based on molecular alterations is crucial. Such classification will provide more accurate and useful diagnostic tools and, eventually, more effective therapeutic options.

One of the most important alterations involved in carcinogenesis is aberrant promoter methylation. The interest in this field has grown due to the implementation of the methylaton specific PCR (MSP) assay. DNA methylation occurs when cytosine is methylated at position 5, this only appears when directly followed by the base guanine in the CpG dinucleotide. This modification has important regulatory effects on gene expression predominantly when it involves CpG rich areas (CpG islands). Methylated cytosines in the promoter regions of a gene lead to its inactivation.

In one aspect the invention provides a novel and accurate method to predict survival of NSCLC patients following cisplatin or carboplatin based chemotherapy, based on the methylation status of nucleic acids of the 14-3-3 sigma gene, particularly those of the promoter sequences. In an embodiment, the methylation status is determined by studying the methylation pattern of the CpG islands in the exon 1 of the 14-3-3 sigma DNA sequence.

The 14-3-3 proteins are a family of highly conserved phosphoserine/phosphothreonine-binding molecules that control the function of a wide array of cellular proteins. They play important roles in a wide range of vital regulatory processes, including signal transduction, apoptosis, cell cycle progression and DNA replication. In mammalian cells, seven 14-3-3 isoforms (beta, gamma, epsilon, eta, sigma, theta and zeta) have been identified and each of these seems to have distinct tissue localizations and isoform-specific functions. 14-3-3σ expression is restricted to epithelial cells. Previous studies have shown that 14-3-3 protein levels are higher in human lung cancers as compared to normal tissues.

Of all the 14-3-3 genes, 14-3-3σ has been most directly linked to cancer (Hermeking H., The 14-3-3 cancer connection. *Nature Rev Cancer* 2003; 3:931-43). It is thought to function as a tumour suppressor by inhibiting cell-cycle progression and by causing cells to leave the stem-cell compartment and undergo differentiation. Inactivation of 14-3-3σ occurs at many levels, and the high frequency of 14-3-3σ inactivation indicates that it has a crucial role in tumour formation.

Surprisingly, we found that NSCLC patients presenting hypermethylation (and therefore silencing) of the 14-3-3 sigma gene are more sensitive to cisplatin or carboplatin chemotherapy and show significantly better survival. This difference in survival is even more pronunciated in patients responding to the chemotherapy.

The method of the invention in its different embodiments will be described now in detail. First a sample tissue or body fluid of a patient suffering from NSCLC is taken. The present method can be applied to any type of tissue or body fluid from a patient.

In one embodiment it is preferable to examine tumor tissue. Preferably this is done prior to the chemotherapy. Tumors or portions thereof are surgically resected from the patient or obtained by routine biopsy. To simplify conservation and handling of the samples, these can be formalin-fixed and paraffin-embedded.

However, from the clinical point of view, the obtention of tissue samples is limited because of the scarcity of tumor tissue obtained by bronchoscopy in stage IV NSCLC patients. In early stages, sometimes we can benefit from the resected tumor specimens that provide tumor tissue for RNA extraction. But a much better alternative is to use body fluids, in particular serum, as the sample.

Genetic analysis has shown that cell-free circulating DNA in plasma or serum of cancer patients shares similar genetic alterations to those described in the corresponding tumor. On one study, a high correlation between methylation of some genes in tumor and serum in glioblastoma patient samples and a good correlation in NSCLC patient samples was found (Ramirez, J L, Tarón, M, et al. Serum DNA as a tool for cancer patient management, *Rocz Akad Med Bialymst*. 2003; 48:34-41).

Therefore, in another aspect of the invention it is preferred that the sample is a body fluid from the NSCLC patient selected from blood, plasma or serum. More preferably it is serum. Serum is easily and immediately available from the patient, it suffices to take a blood sample and separate the cells by centrifugation.

The nucleic acids, preferably DNA, are extracted from the sample by procedures known to the skilled person and commercially available such as the QIAmp Blood Mini kit of QIAGEN.

Once the nucleic acid is isolated, the method of the invention includes determining the state of methylation of one or more of those nucleic acids encoding the gene 14-3-3 sigma and isolated from the subject.

The expressions "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

Any method for determining the methylation state of the nucleic acids can be used, such as those described in WO 02/27019, U.S. Pat. No. 6,017,704, U.S. Pat. No. 6,331,393 and U.S. Pat. No. 5,786,146, each of which is incorporated herein in its entirety. Determining the methylation state of the nucleic acid includes amplifying the nucleic acid by means of oligonucleotide primers that distinguishes between methylated and unmethylated nucleic acids. One of such methods is described in detail in the examples.

Preferably the method for detecting a methylated CpG-containing nucleic acid includes contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. The amplification step is optional and although desirable, is not essential. The method relies on the PCR reaction itself to distinguish between modified (e.g., chemically modified) methylated and unmethylated DNA.

The term "modifies" as used herein means the conversion of an unmethylated cytosine to another nucleotide which will facilitate methods to distinguish the unmethylated from the methylated cytosine. Preferably, the agent modifies unmethylated cytosine to uracil. Preferably, the agent used for modifying unmethylated cytosine is sodium bisulfite, however, other agents that similarly modify unmethylated cytosine, but not methylated cytosine can also be used in the method. Sodium bisulfite ($NaHSO_3$) reacts readily with the 5,6-double bond of cytosine, but poorly with methylated cytosine. Cytosine reacts with the bisulfite ion to form a sulfonate cytosine reaction intermediate that is susceptible to deamination, giving rise to a sulfonate uracil. The sulfonate group can be removed under alkaline conditions, resulting in the formation of uracil. Uracil is recognized as a thymine by Taq polymerase (C→U→T) and therefore upon PCR, the resultant product contains cytosine only at the position where 5-methylcytosine occurs in the starting template DNA (mC→mC→C).

The primers used to determine the methylation state of the 14-3-3 sigma gene are preferably from the promoter region, more preferably from exon 1. The region between CpG dinucleotides 3 and 9 within the 14-3-3σ gene is especially preferred because of the accuracy of the results obtained.

The methylation state can be determined qualitatively or quantitatively. Well known methods such as fluorescence-based quantitative PCR (using fluorescent primers such as Taqman probes) can be used. Further details can be found in U.S. Pat. No. 6,331,393.

In a preferred embodiment a qualitative determination is used, it is quicker and simpler to implement in a lab and the results are accurate. In this embodiment primers able to discriminate between the methylated or unmethylated DNA, as explained before, are used for the PCR, and then the resulting DNA is purified and its methylation status determined for example by separation through agarose gel electrophoresis. A simple visual examination (needs previous staining) under UV light allows to classify the sample as methylated when bands are present in the methylated lane or unmethylated when bands are present in the unmethylated lane only. Synthetically methylated and unmethylated DNA are used as controls.

Once the methylation status from a sample is obtained, survival can be predicted in accordance with the results shown in the examples. Patients with methylation status will have improved time to progression and survival if treated with cisplatin or carboplatin chemotherapy. Survival time ranges can be predicted to be in average at least 30% longer for methylated patients.

Following chemotherapy, the prediction can be further improved once it is known if the patient belongs to the "responder" group. If so, the chance of survival after four months can be predicted to be at least five times higher for methylation-positive responders than for methylation-negative responders, and survival time ranges in general can be predicted to be in average at least 50% longer for 14-3-3-sigma methylated patients.

As used herein, "a clinical response" is the response of the tumor to treatment with a chemotherapeutic agent. Criteria for determining a response to therapy are widely accepted and enable comparisons of the efficacy alternative treatments. A complete response (or complete remission) is the disappearance of all detectable malignant disease. A partial response is an approximately 50 percent decrease in the product of the greatest perpendicular diameters of one or more lesions, no new lesions and no progression of any lesion. A responder is a patient giving a complete or partial response to the cisplatin or carboplatin chemotherapy.

In accordance with another embodiment of the present invention, there is provided a kit for predicting the survival to chemotherapeutic treatment of NSCLC in a subject. Invention kits include a first container containing a reagent which modifies unmethylated cytosine and a second container containing primers for amplification of a CpG-containing nucleic acid, of the 14-3-3 gene, wherein the primers distinguish between modified methylated and nonmethylated nucleic acid. Preferably, the reagent that modifies unmethylated cytosine is bisulfite.

The invention being thus described, practice of the invention is illustrated by the experimental examples provided below. These examples should not be interpreted as limiting the scope of the claims.

EXAMPLES

A multicenter prospective study to assess 14-3-3σ methylation in the sera of advanced non-small-cell lung cancer patients and correlate methylation status with survival was carried out. The study was approved by the independent ethics committees of all six participating centers, and all patients gave their signed informed consent.

Patients

Patients were considered eligible for the present study if they had stage IV or stage IIIB (with malignant pleural effusion) histologically confirmed non-small-cell lung cancer. Other criteria for eligibility included an Eastern Cooperative Oncology Group (ECOG) performance status of 0 (asymptomatic and fully active) or 1 (symptomatic, fully ambulatory, restricted in physically strenuous activity); age of at least 18 years; adequate hematologic function (hemoglobin at least 9 g per deciliter [5.6 mmol per liter], neutrophil count at least 1500 per cubic millimeter, and platelet count at least 100,000 per cubic millimeter); adequate renal function (serum creatinine less than 1.5 times the upper limit of normal); and adequate liver function (bilirubin not more than 1.5 times the upper limit of normal, aspartate aminotransferase and alanine aminotransferase not more than 5 times the upper limit of normal). Patients with clinically overt brain metastases and those who had received previous chemotherapy were excluded. Patients with ECOG performance status of 2 (symptomatic, ambulatory, capable of self-care, more than 50 percent of waking hours spent out of bed) were also excluded, based on results of previous studies where these patients had a high rate of serious adverse events and poor survival.

Patients received cisplatin at a dose of 75 mg per square meter of body-surface area on day 1 plus gemcitabine at a dose of 1250 mg per square meter on days 1 and 8. The cycle was repeated every 3 weeks for a maximum of six cycles.

Before the study, all patients underwent staging procedures, including a clinical examination, a two-view chest x-ray, and a computed tomography of the thorax and abdomen. Bone scan or computed tomographic scan of the brain was required only for patients with suspected bone or brain metastases. Before each administration of chemotherapy, patients underwent a clinical examination consisting of a routine biochemistry workup and blood counts.

Objective responses were evaluated by clinical investigators after the third and sixth treatment cycles by repeating the staging procedures. A complete response was defined as the disappearance of all known sites of disease; a partial response was defined as a decrease of 50 percent or more in the sum of the products of the largest perpendicular diameters of measurable lesions, no new lesions, and no progression of any lesion; stable disease was defined as a decrease of less than 50 percent or an increase of less than 25 percent in the sum of the products of the largest perpendicular diameters of measurable lesions and no new lesions; and progressive disease was defined as an increase of 25 percent or more in the size of one or more measurable lesions, or a new lesion. For the evaluation of response, patients achieving complete or partial response were considered "responders", and all other patients were considered "non-responders". Time to progression was calculated from the date of enrollment to the date of progression. Survival was calculated from the date of enrollment to the date of death or last clinical follow-up.

Methylation-Specific Polymerase Chain Reaction Analysis of 14-3-3σ

Ten milliliters of peripheral blood were collected in clot activator tubes, and serum was separated from cells by centrifugation. Samples were sent to our laboratory (Catalan Institute of Oncology, Barcelona, Spain) for 14-3-3σ methylation analysis. DNA was extracted from 800 microliters of serum using QIAmp DNA Mini blood kit (Qiagen, Valencia, Calif., USA) and resuspended in a final volume of 50 microliters. Paired tumor and serum DNA from an independent group of 28 surgically resected non-small-cell lung cancer patients was used as control. Tumor genomic DNA was also derived from paraffin-embedded resected tumor tissue obtained by laser capture microdissection (Palm, Oberlensheim, Germany). Isolated tumor DNA was incubated with proteinase K, and DNA was extracted with phenol-chloroform and ethanol precipitation. Purified serum or tumor DNA was denatured with sodium hydroxide and modified with sodium bisulfite, which converts unmethylated, but not methylated, cytosines to uracil.

Methylation-specific polymerase chain reaction was performed with primers specific for either methylated or the modified unmethylated DNA spanning the region between CpG dinucleotides 3 and 9 within the 14-3-3σ gene (FIG. 1). DNA samples were then purified with the Wizard DNA purification resin (Promega, Madison, Wis., USA), again treated with sodium hydroxide, precipitated with ethanol, and resuspended in water. Primers specific for methylated DNA [5'-GATATGGTAGTTTTTATGAAAGGCGTCG-3' (sense) and 5'-CCTCTAACCGCCCACCACG-3' (antisense)], and primers specific for unmethylated DNA [5'-GATATGG-TAGTTTTTATGAAAGGTGTTGTG-3' (sense) and 5'-CCCTCTAACCACCCACCACA-3' (antisense)] yielded a 109 bp polymerase chain reaction product. The polymerase chain reaction conditions were as follows: 1 cycle of 95° C. for 12 minutes; 45 cycles of 95° C. for 30 seconds, 58° C. (unmethylated reaction) or 64° C. (methylated reaction) for 30 seconds, 72° C. for 30 seconds; and 1 cycle of 72° C. for 7 minutes.

Figure 2:
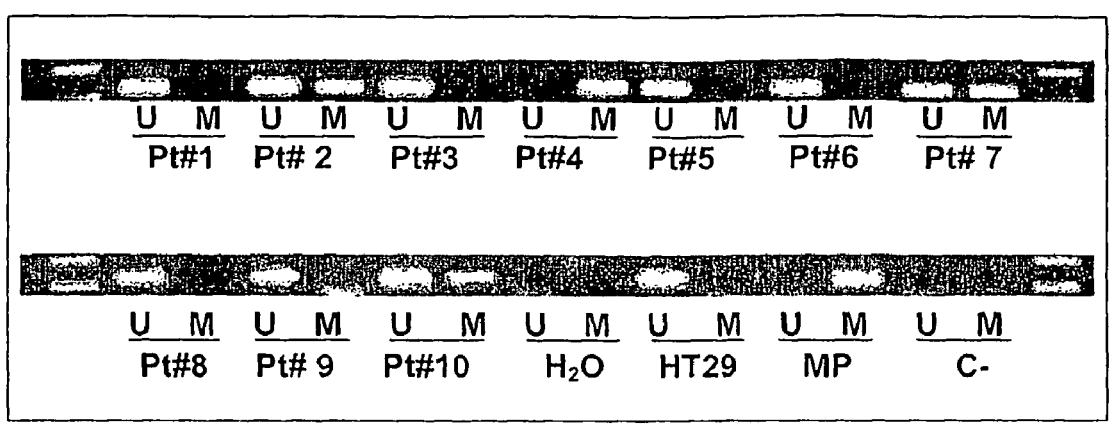
FIG. 2. Methylation specific polymerase chain reaction for 14-3-3σ. Methylation was detected in DNA extracted from serum using the QIAmp Blood Mini kit (QIAGEN, Valencia, Calif., USA), according to the manufacturer's protocol. Sodium bisulfite modification was performed, and 5 µl of the resulting DNA was subjected to polymerase chain reaction amplification using primers specific for either unmethylated (U) or methylated (M) 14-3-3σ. Bisulfite-modified human colorectal cancer cell line (HT29 [American Type Culture Collection, Manassas, Va., USA]) (U) was used as normal unmethylated control, while in vitro SssI bisulfite-modified placental DNA (M) used as positive methylated control. No template controls (C—) were also subjected to polymerase chain reaction as contamination controls. Samples were scored as methylation-positive when methylated alleles were present, visualized as bands in the methylated DNA lane (patients 2, 4, 7, 10) and as methylation-negative when bands were seen only in the unmethylated DNA lane (patients 1, 3, 5, 6, 8, 9).

Placental DNA treated in vitro with Sss I methyltransferase (New England Biolabs, Beverly, Mass., USA) was used as a positive control for methylated alleles of 14-3-3σ, and DNA from normal lymphocytes was used as a negative control. Ten microliters of each 50-microliter methylation-specific amplified product was loaded directly onto non-denaturing 2 percent agarose gels, stained with ethidium bromide, and examined under ultraviolet illumination. Samples were scored as methylation-positive when methylated alleles were present, visualized as bands in the methylated DNA lane (FIG. 2), and as methylation-negative when bands were seen only in the unmethylated DNA lane (FIG. 2).

Statistical Analyses

Survival from the date of enrollment was the main endpoint. Assuming a two-sided level of significance of 0.05, an initial sample size of 121 patients was calculated to provide a power of 90 percent to detect a 15 percent increase in survival at one year in the methylation-positive group (Parmar M K B, Machin D. Sample sizes for survival studies. In Parmar M K B, Machin D, eds. Survival analysis. A practical approach. Chichester, UK: John Wiley & Sons, 1996:196-207). Analyses were carried out over a total of 115 patients. Survival times according to 14-3-3σ methylation status were estimated with the Kaplan-Meier method and compared with the two-sided log-rank test. Baseline characteristics and response according to 14-3-3σ methylation status were compared with either the two-sided Fisher's exact test or the Chi-square test for categorical variables and with the student's t-test for age. The normality of age was verified with a Kolmogorov-Smirnov test. Correlation between response and other variables was assessed with a two-sided Fisher's exact test. Univariate and multivariate logistic regression models were fitted to obtain crude and adjusted odds ratios for methylation status. The Hosmer-Lemeshow likelihood test was used to assess the goodness of fit. A univariate Cox regression analysis was used to assess the association between each potential prognostic factor and survival and time to progression. Factors found to be relatively significant ($P<0.1$) in the univariate analysis were included in a multivariate Cox proportional-hazards regression model with a stepwise procedure (both forward and backward) to evaluate the independent significance of different variables on survival. The likelihood ratio test was used to assess the goodness of fit, and the Wald's test was used to assess the coefficient significance. The relative risk and 95 percent confidence intervals were calculated from the Cox model for all significant predictors of the time to event. Estimates of the time to event, with associated 95 percent confidence intervals were made according to the cumulative incidence method. A landmark analysis, with a landmark time of four months, was used to evaluate the association of response with survival. Multivariate analysis was performed using the Cox regression model stratified by response, with 14-3-3σ methylation status adjusted by performance status. For all regression analyses, the assumptions of the Cox model were tested and met. Statistical significance was set at 0.05. Analyses were performed using SPSS 11.0 for calculations and S-PLUS 6.1 for plots.

Results

A total of 115 patients were enrolled in this study between Aug. 1, 2001 and Jun. 30, 2002. The median follow-up of patients still alive at the time of analysis was 17 months (range, 1-30.7). Median age was 62 years (range, 31-81);

male, 108 (93.9 percent); ECOG performance status 0, 32 (27.8 percent), 1, 83 (72.2 percent); smokers, 99 (86.1 percent); adenocarcinoma, 51 (44.7 percent), squamous cell carcinoma, 42 (36.8 percent), large cell carcinoma, 21 (18.4 percent). Twenty-five patients (21.7 percent) had malignant pleural effusion, and eight (7 percent) had undergone prior surgery of the primary lung tumor. No patient received thoracic radiotherapy. Characteristics for all 115 patients are shown in Table 1.

Representative results of the methylation-specific polymerase chain reaction analysis are shown in Table 1. Thirty-nine patients were 14-3-3σ methylation-positive and 76 were 14-3-3σ methylation-negative. Demographic and clinical characteristics were well-balanced between these two groups (Table 1). Of 28 surgically resected patients used as controls, seven were methylation-positive in both tumor and serum and the remaining 21 were methylation-negative in both tumor and serum.

TABLE 1

Patient characteristics for all 115 patients and broken down according to 14-3-3σ methylation status.

|  | Total | 14-3-3σ Methylation-Negative | 14-3-3σ Methylation-Positive |
|---|---|---|---|
| No. Patients | 115 | 76 | 39 |
| Age |  |  |  |
| Median | 62 | 63 | 61 |
| Range | 31-81 | 40-81 | 31-78 |
| Sex |  |  |  |
| Male | 108 (93.95%) | 70 (92.1%) | 38 (97.4%) |
| Female | 7 (6.1%) | 6 (7.9%) | 1 (2.6%) |
| Smoking status |  |  |  |
| Smoker | 99 (86.1%) | 64 (84.2%) | 35 (89.7%) |
| Non-smoker | 16 (13.9%) | 12 (15.8%) | 4 (10.3%) |
| ECOG performance status |  |  |  |
| 0 | 32 (27.8%) | 21 (27.6%) | 11 (28.2%) |
| 1 | 83 (72.2%) | 55 (72.4%) | 28 (71.8%) |
| Histology |  |  |  |
| Adenocarcinoma | 51 (44.3%) | 38 (50%) | 13 (33.3%) |
| Squamous cell carci. | 42 (36.5%) | 23 (30.3%) | 19 (48.7%) |
| Large cell carcinoma | 22 (19.1%) | 15 (19.7%) | 7 (17.9%) |
| Pleural Effusion |  |  |  |
| Yes | 25 (21.7%) | 16 (21.1%) | 9 (23.1%) |
| No | 90 (78.3%) | 60 (78.9%) | 30 (76.9%) |
| Prior Surgery |  |  |  |
| Yes | 8 (7%) | 5 (6.6%) | 3 (7.7%) |
| No | 107 (93%) | 71 (93.4%) | 36 (92.3%) |
| Response |  |  |  |
| Complete response | 2 (1.7%) | 2 (2.6%) | 0 |
| Partial response | 49 (42.6%) | 27 (35.5%) | 22 (56.4%) |
| Stable disease | 27 (23.5%) | 22 (28.9%) | 5 (12.8%) |
| Progressive disease | 37 (32.2%) | 25 (32.9%) | 12 (30.8%) |

Tumor Response

One hundred and fifteen patients were assessable for response. Two patients (1.7 percent) attained complete response; 49 (42.6 percent) had partial response; 27 (23.5 percent) had stable disease; and 37 (32.2 percent) had progressive disease. The univariate regression model showed that only ECOG performance status correlated significantly with response (crude odds ratio:performance status 0, 2.33 [95 percent confidence interval, 1.01-5.36]; P=0.05). The crude odds ratio for 14-3-3σ methylation-positive status was 2.10 (95 percent confidence interval, 0.96-4.59) (P=0.06).

Time to Progression

Overall time to progression for all 115 patients was 6.9 months (95 percent confidence interval, 5.3-8.5). Time to progression was 6.3 months (95 percent confidence interval, 4.5-8.2) for the methylation-negative group and 8.0 months (95 percent confidence interval, 5.3-10.7) for the methylation-positive group (P=0.027 by the two-sided log-rank test).

The univariate Cox regression model showed that only 14-3-3σ methylation status significantly correlated with time to progression (hazard ratio: 14-3-3σ methylation-negative status, 1.59 [95 percent confidence interval, 1.05-2.40]; P=0.029). A stepwise multivariate Cox proportional-hazards regression model identified only 14-3-3σ methylation status as an independent prognostic factor for time to progression. Sixty-four patients (55.7 percent) did not receive second-line chemotherapy. Of the 51 remaining patients (44.3 percent) who received second-line chemotherapy, 32 (62.7 percent) were methylation-negative and 19 (37.3 percent) were methylation-positive.

Survival

Median survival for all 115 patients was 10.9 months (95 percent confidence interval, 8.6-13.2). Median survival was 9.8 months (95 percent confidence interval, 7.3-12.5) for the methylation-negative group, compared to 15.1 months (95 percent confidence interval, 9.7-20.6) for the methylation-positive group (P=0.004 by the two-sided log-rank test) (FIG. 4A). The univariate Cox regression model showed that only 14-3-3σ methylation status and ECOG performance status significantly correlated with survival (hazard ratios: 14-3-3σ methylation-negative status, 2.07 [95 percent confidence interval, 1.24-3.45; P=0.006]; performance status 1, 2.45 [95 percent confidence interval, 1.39-4.32; P=0.002] (Table 2). The stepwise multivariate Cox regression model also identified only 14-3-3σ methylation status and ECOG performance status as independent prognostic markers for survival.

Survival According to Tumor Response and 14-3-3σ Methylation Status

The univariate Cox regression model including all 115 patients showed that in addition to 14-3-3σ methylation status and ECOG performance status, response also significantly correlated with survival (hazard ratio for non-responders, 2.84 [95 percent confidence interval, 1.75-4.60; P<0.001) (Table 2).

TABLE 2

Correlation of pre-treatment characteristics and response with survival, in 115 patients by univariate analysis.

|  | No. Patients | Hazard Ratio | P |
|---|---|---|---|
| 14-3-3σ status |  |  | 0.006 |
| Methylation-positive | 39 | 1 referent |  |
| Methylation-negative | 76 | 2.07 (1.24-3.45) |  |
| Response |  |  | <0.001 |
| Responders | 51 | 1 referent |  |
| Non-responders | 64 | 2.84 (1.75-4.60) |  |
| ECOG performance status |  |  | 0.002 |
| 0 | 32 | 1 referent |  |
| 1 | 83 | 2.45 (1.39-4.32) |  |
| Prior Surgery |  |  | 0.99 |
| No | 107 | 1 referent |  |
| Yes | 8 | 1.01 (0.44-2.33) |  |
| Smoker |  |  | 0.09 |
| No | 16 | 1 referent |  |
| Yes | 99 | 2.08 (0.90-4.80) |  |
| Pleural Effusion |  |  | 0.97 |
| No | 90 | 1 referent |  |

TABLE 2-continued

Correlation of pre-treatment characteristics and response with survival, in 115 patients by univariate analysis.

| | No. Patients | Hazard Ratio | P |
|---|---|---|---|
| Yes | 25 | 0.99 (0.56-1.74) | |
| Histology | | | |
| Adenocarcinoma | 51 | 1 referent | |
| Squamous cell carcinoma | 42 | 0.90 (0.54-1.50) | 0.68 |
| Large cell carcinoma | 22 | 1.38 (0.77-2.48) | 0.29 |
| Sex | | | 0.26 |
| Female | 7 | 1 referent | |
| Male | 108 | 1.96 (0.62-6.21) | |
| Age | 115 | 0.99 (0.98-1.02) | 0.95 |

Further exploratory analyses were thus carried out to investigate the possible influence on survival of tumor response and methylation status. A landmark analysis which excluded 16 patients who had died before the landmark time of four months found that in the remaining 99 patients, response remained significant for improved survival (hazard ratio for non-responders, 2.16 [95 percent confidence interval, 1.29-3.61]; P=0.03). The univariate Cox regression model showed that only 14-3-3σ methylation status, ECOG performance status and response significantly correlated with survival in these 99 patients (hazard ratios: 14-3-3σ methylation-negative status, 1.99 [95 percent confidence interval, 1.13-3.51; P=0.017]; performance status 1, 2.17 [95 percent confidence interval, 1.19-3.95; P=0.012]; non-responders, 2.68 [95 percent confidence interval, 1.65-4.37; P<0.001). Moreover, a multivariate Cox proportional-hazards regression model that included response, methylation status and performance status and also allowed for their second-order interactions identified 14-3-3σ methylation status, ECOG performance status and response at the selected landmark of four months as independent prognostic factors for survival (Table 3).

TABLE 3

Multivariate analysis after stepwise procedure (forward and backward) in 99 patients with a landmark time of 4 months.

| | No. Patients | Hazard Ratio | P |
|---|---|---|---|
| 14-3-3σ status | | | 0.001 |
| Methylation-positive | 36 | 1 referent | |
| Methylation-negative | 63 | 4.66 (1.83-11.84) | |
| Response | | | 0.001 |
| Responders | 51 | 1 referent | |
| Non-responders | 48 | 5.53 (2.03-15.02) | |
| ECOG performance status | | | 0.003 |
| 0 | 31 | 1 referent | |
| 1 | 68 | 2.54 (1.38-4.70) | |
| 14-3-3σ status by Response | 99 | 0.21 (0.07-0.67) | 0.009 |

Patients were then stratified by response and two separate Cox regression models were fitted, adjusting 14-3-3σ methylation status by performance status. A significant difference in risk of death was observed only in the responder group, where the risk of death for 14-3-3σ methylation-negative responders was almost five times that of methylation-positive responders (hazard ratio=4.87 [95 percent confidence interval, 1.88-12.61]; P=0.001 by the Cox model) (Table 4).

TABLE 4

Correlation of 14-3-3σ methylation status, response and ECOG performance status with survival, by multivariate analysis stratifying by response when 14-3-3σ is adjusted by ECOG performance status over 99 patients after setting a landmark time of 4 months.

| | No. Patients | | P |
|---|---|---|---|
| | | Responders Hazard Ratio | |
| 14-3-3σ status | | | |
| Methylation-positive | 22 | 1 referent | 0.001 |
| Methylation-negative | 29 | 4.87 (1.88-12.61) | |
| ECOG performance status | | | 0.075 |
| 0 | 19 | 1 referent | |
| 1 | 32 | 2.21 (0.92-5.28) | |
| | | Non-Responders Hazard Ratio | |
| 14-3-3σ status | | | |
| Methylation-positive | 14 | 1 referent | 0.992 |
| Methylation-negative | 34 | 0.99 (0.49-2.05) | |
| ECOG performance status | | | 0.018 |
| 0 | 12 | 1 referent | |
| 1 | 36 | 2.93 (1.20-7.17) | |

Figure 3:
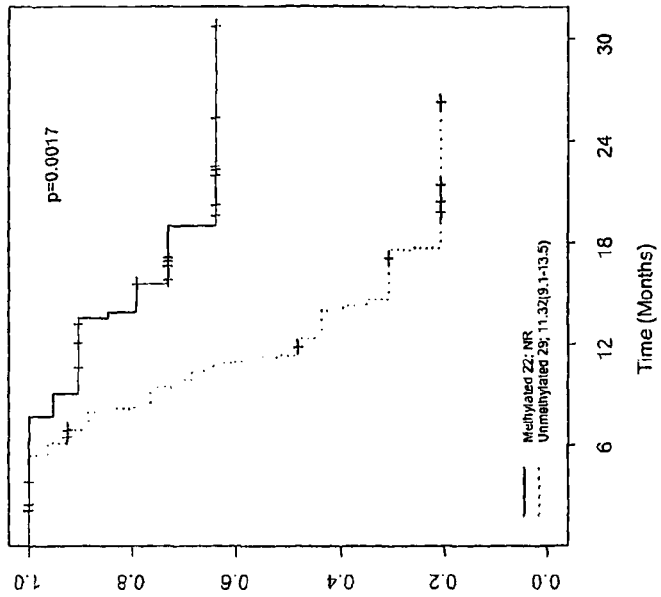
FIG. 3. A shows the Kaplan-Meier probability of survival for all patients. For the methylation-negative group, estimated percent survival rates are: at 6 months, 50 percent (95 percent confidence interval, 60-81 percent); at 12 months, 36 percent (95 percent confidence interval, 26-49 percent); at 18 months, 20 percent (95 percent confidence interval, 12-32 percent). For the methylation-positive group, estimated percent survival rates are: at 6 months, 87 percent (95 percent confidence interval, 77-98 percent); at 12 months, 62 percent (95 percent confidence interval, 48-80 percent); at 18 months, 41 percent (95 percent confidence interval, 27-63 percent). B shows the Kaplan-Meier probability of survival for responders. For the methylation-negative group, estimated percent survival rates are: at 6 months, 93 percent (95 percent confidence interval, 83-100 percent); at 12 months, 44 percent (95 percent confidence interval, 28-69 percent); at 18 months, 21 percent (95 percent confidence interval, 9-47 percent). For the methylation-positive group, estimated percent survival rates are: at 6 months, 95 percent (95 percent confidence interval, 87-100 percent); at 12 months, 85 percent (95 percent confidence interval, 70-100 percent); at 18 months, 64 percent (95 percent confidence interval, 44-94 percent). CI=confidence interval.
Figure 3:
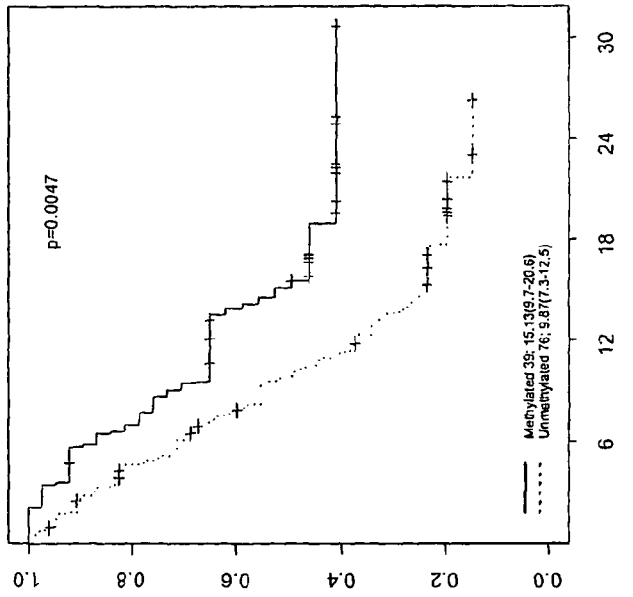

Kaplan-Meier curves for survival of responders according to 14-3-3σ methylation status showed that median survival for 22 14-3-3σ methylation-positive responders has not been reached, while for 29 14-3-3σ methylation-negative responders, it was 11.3 months (95 percent confidence interval, 9.0-13.5) (P=0.001 by the two-sided log-rank test) (FIG. 3B). The estimated survival rate at 18 months is 64 percent (95 percent confidence interval, 44-94 percent) for methylation-positive responders and 21 percent (95 percent confidence interval, 9-47 percent) (P=0.017 by the two-sided log-rank test) for methylation-negative responders. Methylation-negative responders had a four times greater risk of death than methylation-positive responders (hazard ratio=3.95 [95 percent confidence interval, 1.57-9.94]; P=0.004 by the Cox model).

The invention claimed is:

1. A method for treating a patient suffering from NSCLC the method comprising the steps of determining the methylation state of a nucleic acid encoding 14-3-3 sigma in a biological sample from the patient, and administering cisplatin or carboplatin chemotherapy to the patient if methylation is detected in said sample.

2. The method of claim 1, wherein the methylation state of the nucleic acid is determined in the regulatory region of the nucleic acid.

3. The method of claim 2, wherein the regulatory region is the promoter region of the 14-3-3 sigma gene.

4. The method according to claim 3, wherein the promoter region is the exon 1 of the 14-3-3 sigma gene.

5. The method according to claim 1, wherein the nucleic acid is isolated from a tumor sample of the patient.

6. A method according to claim 1, wherein the nucleic acid is isolated from a serum sample of the patient.

7. The method according to claim 1, wherein the cisplatin based chemotherapeutic regimen is selected from cisplatin or carboplatin as single agents or a combination selected from cisplatin/paclitaxel, cisplatin/gemcitabine, cisplatin/docetaxel and carboplatin/paclitaxel.

* * * * *

SEQUENCE LISTING

<160> NUMBER OF SEQ ID NOS: 5

<210> SEQ ID NO 1
<211> LENGTH: 248
<212> TYPE: DNA
<213> ORGANISM: Homo sapiens

<400> SEQUENCE: 1
atggagagag ccagtctgat ccagaaggcc aagctggcag agcaggccga acgctatgag    60

```
gacatggcag ccttcatgaa aggcgccgtg gagaagggcg aggagctctc ctgcgaagag    120
cgaaacctgc tctcagtagc ctataagaac gtggtgggcg gccagagggc tgcctggagg    180
gtgctgtcca gtattgagca gaaaagcaac gaggagggct cggaggagaa ggggcccgag    240
gtgcgtga                                                             248

<210> SEQ ID NO 2
<211> LENGTH: 28
<212> TYPE: DNA
<213> ORGANISM: Artificial
<220> FEATURE:
<223> OTHER INFORMATION: Sense Primer Specific for Methylated DNA
      Designed to Amplify DNA of 14-3-3 Sigma Gene

<400> SEQUENCE: 2
gatatggtag tttttatgaa aggcgtcg                                        28

<210> SEQ ID NO 3
<211> LENGTH: 19
<212> TYPE: DNA
<213> ORGANISM: Artificial
<220> FEATURE:
<223> OTHER INFORMATION: Antisense primer specific for methylated DNA
      designed to amplify DNA of 14-3-3 Sigma Gene

<400> SEQUENCE: 3
cctctaaccg cccaccacg                                                  19

<210> SEQ ID NO 4
<211> LENGTH: 30
<212> TYPE: DNA
<213> ORGANISM: Artificial
<220> FEATURE:
<223> OTHER INFORMATION: Sense primer specific for unmethylated DNA
      designed to amplify DNA of 14-3-3 Sigma Gene

<400> SEQUENCE: 4
gatatggtag tttttatgaa aggtgttgtg                                      30

<210> SEQ ID NO 5
<211> LENGTH: 20
<212> TYPE: DNA
<213> ORGANISM: Artificial
<220> FEATURE:
<223> OTHER INFORMATION: Antisense primer specific for unmethylated DNA
      designed to amplify DNA of 14-3-3 Sigma Gene

<400> SEQUENCE: 5
ccctctaacc acccaccaca                                                 20
```